(12) United States Patent
Silbersweig et al.

(10) Patent No.: US 11,630,176 B2
(45) Date of Patent: Apr. 18, 2023

(54) SYSTEM AND METHOD FOR CONTROLLING PHYSIOLOGICAL NOISE IN FUNCTIONAL MAGNETIC RESONANCE IMAGING

(71) Applicant: The Brigham and Women's Hospital, Inc., Boston, MA (US)

(72) Inventors: David Silbersweig, Boston, MA (US); Emily Stern, Boston, MA (US); Hong Pan, Boston, MA (US); Qiang Chen, Baltimore, MD (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 17/788,340

(22) PCT Filed: Dec. 23, 2020

(86) PCT No.: PCT/US2020/066921
§ 371 (c)(1),
(2) Date: Jun. 23, 2022

(87) PCT Pub. No.: WO2021/133961
PCT Pub. Date: Jul. 1, 2021

(65) Prior Publication Data
US 2023/0023393 A1    Jan. 26, 2023

Related U.S. Application Data

(60) Provisional application No. 62/953,686, filed on Dec. 26, 2019.

(51) Int. Cl.
G06K 9/00    (2022.01)
G01R 33/48   (2006.01)
(Continued)

(52) U.S. Cl.
CPC ....... *G01R 33/4806* (2013.01); *G01R 33/565* (2013.01); *A61B 5/055* (2013.01)

(58) Field of Classification Search
CPC .... G01R 33/4806; G01R 33/565; A61B 5/055
(Continued)

(56) References Cited

U.S. PATENT DOCUMENTS

| 6,073,041 A * | 6/2000 | Hu | G01R 33/4806 324/309 |
|---|---|---|---|
| 2003/0153826 A1* | 8/2003 | Jack | A61B 5/7207 600/410 |

(Continued)

OTHER PUBLICATIONS

Chuang, K.-H. and Chen, J.-H. (2001), IMPACT: Image-based physiological artifacts estimation and correction technique for functional MRI. Magn. Reson. Med., 46: 344-353. https://doi.org/10.1002/mrm.1197 (Year: 2001).*

(Continued)

*Primary Examiner* — Van D Huynh
(74) *Attorney, Agent, or Firm* — Quarles & Brady LLP

(57) ABSTRACT

A system and method is provided for controlling physiological-noise in functional magnetic resonance imaging using raw k-space data to extract physiological noise effects. The method can identify these effects when they are separable and directly reflects the artefactual effects on fMRI data, without the need for external monitoring or recording devices and to be compensated for via rigorous statistical analysis modeling of such noise sources. The physiological fluctuations may be treated as global perturbations presented around the origin point in a k-space 2D slice. Each k-space 2D slice may be acquired at a very short repetition time with an effective sampling rate to sample cardiac and respiratory rhythms through proper reordering and phase-unwarping techniques applied to the raw k-space data.

31 Claims, 6 Drawing Sheets

(51) Int. Cl.
*G01R 33/565* (2006.01)
*A61B 5/055* (2006.01)

(58) Field of Classification Search
USPC ......................................................... 382/128
See application file for complete search history.

(56) References Cited

U.S. PATENT DOCUMENTS

| | | | | |
|---|---|---|---|---|
| 2009/0028411 A1* | 1/2009 | Pfeuffer | ........... | G01R 33/56509 324/307 |
| 2012/0235679 A1* | 9/2012 | Xue | ................ | G01R 33/56509 324/307 |
| 2012/0249138 A1* | 10/2012 | Pfeuffer | ........... | G01R 33/56563 324/309 |
| 2013/0144140 A1* | 6/2013 | Frederick | ............. | A61B 5/0075 600/324 |
| 2014/0126796 A1* | 5/2014 | Chesneau | .......... | G01R 33/4824 382/131 |
| 2015/0268324 A1* | 9/2015 | Zhai | ................. | G01R 33/56509 324/309 |
| 2015/0309147 A1* | 10/2015 | Schmitter | ............ | G01R 33/443 600/410 |
| 2019/0086494 A1* | 3/2019 | Pfeuffer | ............. | G01R 33/4818 |

OTHER PUBLICATIONS

Hu, X., Le, T.H., Parrish, T. and Erhard, P. (1995), Retrospective estimation and correction of physiological fluctuation in functional MRI. Magn. Reson. Med., 34: 201-212. https://doi.org/10.1002/mrm.191034021 (Year: 1995).*

International Search Report of International Application No. PCT/US20/66921, dated Apr. 29, 2021, 2 pages.

Written Opinion of International Application No. PCT/US20/66921, dated Apr. 29, 2021, 6 pages.

Pfeuffer, Jr. et al., Correction of physiologically induced global off-resonance effects in dynamic echo-planar and spiral functional imaging; (2002) Magnetic Resonance in Medicine 47:344-353, entire document; https://doi.org/10.1002/mrm.10065.

* cited by examiner

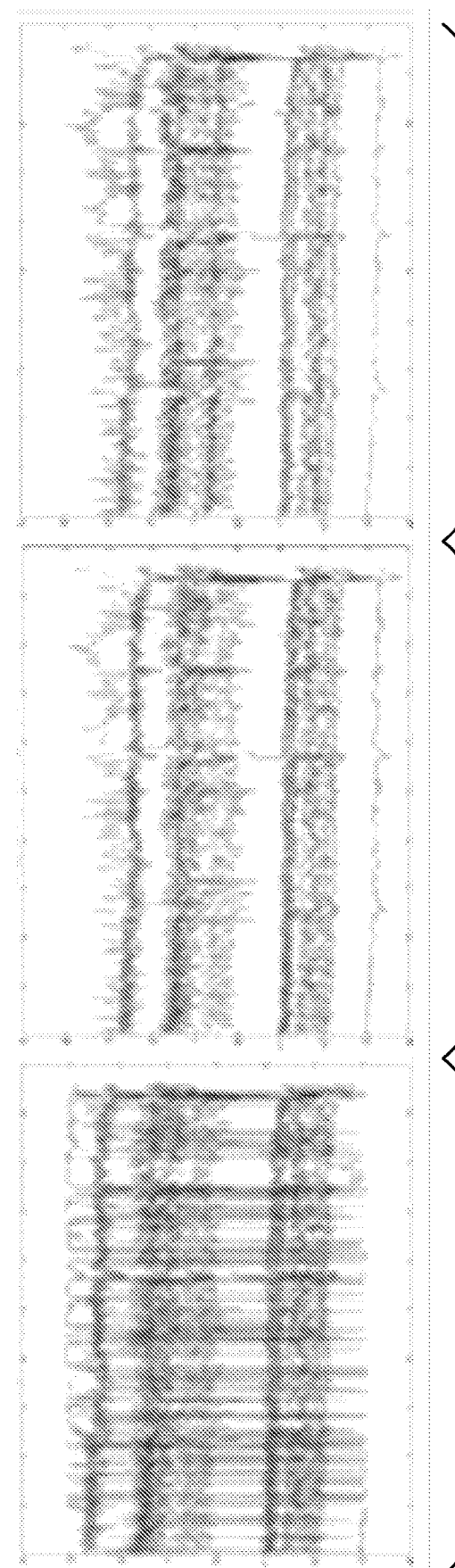
FIG. 3A
FIG. 3B
FIG. 3C

SYSTEM AND METHOD FOR CONTROLLING PHYSIOLOGICAL NOISE IN FUNCTIONAL MAGNETIC RESONANCE IMAGING

CROSS-REFERENCE TO RELATED APPLICATIONS

This application is a 371 application of PCT/US2020/066921 filed Dec. 23, 2020, which claims the benefit of U.S. Provisional Patent Application Ser. No. 62/953,686 filed on Dec. 26, 2019 and entitled "System and Method for Controlling Physiological Noise in Functional Magnetic Resonance Imaging," the entire disclosure of which is incorporated herein by reference as set forth in its entirety for all purposes.

STATEMENT REGARDING FEDERALLY SPONSORED RESEARCH

N/A

BACKGROUND

Increasing the signal-to-noise (SNR) ratio is a fundamental goal in radiological imaging. Improved data quality leads to images that are qualitatively easier to evaluate, with the ability to detect more subtle abnormalities. For imaging modalities that are quantitative or semi-quantitative in nature, increasing SNR allows analysis algorithms to return more accurate results. An additional benefit is the potential for decreased scanning time, since adequate SNR for interpretable images is achieved more quickly.

In MRI, there are multiple sources of noise that can degrade images, resulting in decreased SNR. In the brain, motion effects due to pulsation of local blood vessels, especially larger vessels near the base of the brain, causes internal motion artifacts. Respiration can also cause internal motion effects. These effects become even more pronounced with the use of fast MRI acquisition sequences, such as echo-planar imaging (EPI). Neither of these sources of physiological noise are routinely removed from brain MRI. For functional MRI (fMRI), the signals being measured (often blood-oxygen-level-dependent [BOLD] changes), can be quite small, especially in relation to the multiple sources of noise that are present with this imaging modality in addition to physiological motion effects (e.g. external head motion, susceptibility effects, etc). For example, for subtle BOLD changes, the noise effects from physiological sources alone can be as large as the desired signal. Quantitative or semi-quantitative analyses can therefore return grossly inaccurate results. In certain fMRI applications, such as the study of subtle cognitive, emotional, and behavioral functional anatomy, and of diseases that affect these functions such as psychiatric disease, critical signal is located near the base of the brain. This area is particularly prone to physiological noise artifacts due to proximity to the Circle of Willis and its adjacent vasculature. For the above reasons, removal of physiological noise is critical.

From a statistical point of view, structured noise patterns from 4D fMRI data (especially confounding physiological noise over time) in real world applications remains one of the major sources for spurious activations and connectivity patterns in statistical analyses of fMRI data, due to the fact that any structured temporal noise pattern, if not detected and modeled accordingly, will lead to biased effect estimation, large residual variance, and model assumption violations. However, all MRI systems acquire data, including fMRI data, in k-space. This k-space data may then be reconstructed into real-space images in an online process with scanner computing servers. Typically, only the real-space images are then transferred to an offline file server, such as a picture archive system (PACS). In doing so, noise information is mostly lost in real-space images reconstructed by the scanner server, and cannot be recovered with conventional offline computation.

Thus there remains a need for making fMRI a reliable and practical instrument for diagnosing individual patients with neurological and psychiatric disorders where noise is addressed at the stage of fMRI data acquisition in a manner with built-in procedures in subsequent image processing and statistical analyses.

SUMMARY OF THE DISCLOSURE

The present disclosure addresses the aforementioned drawbacks by providing a system and method for controlling physiological noise in magnetic resonance (MR) imaging, such as functional magnetic resonance imaging (fMRI), using raw k-space data to extract physiological noise effects. The method can identify these effects when they are separable and directly reflects the artefactual effects on the MRI data, without the need for external monitoring or recording devices and to be compensated for via rigorous statistical analysis modeling of such noise sources. In some configurations, the only required additional operation in an MRI scanner environment is to transfer the k-space raw data out of the scanner computing/reconstruction server onto an offline file server. In some configurations, the physiological fluctuations may be treated as global perturbations presented around the origin point in a k-space 2D slice. In some configurations, each 2D slice may be acquired at a very short repetition time (compared to the 3D volume) with an effective sampling rate to sample cardiac and respiratory rhythms through proper reordering and phase-unwarping techniques applied to the raw k-space data.

In one configuration, a method is provided for controlling physiologically-induced noise in magnetic resonance imaging (MRI) data. The method includes acquiring MRI k-space data of a subject with a repetition time that samples physiological motion and determining global physiological fluctuation parameters by extracting an origin point pixel value in a phase image generated from the acquired k-space data. The method also includes extracting physiological noise from the k-space data that was physiologically-induced by the subject using the global physiological fluctuation parameters. The physiological noise may be removed from the MRI data prior to reconstructing an image.

In one configuration, a system is provided for controlling physiologically-induced noise in magnetic resonance imaging (MRI) data. The system includes a computer system configured to: a) acquire MRI k-space data of a subject with a repetition time that samples physiological motion; b) determine global physiological fluctuation parameters by extracting an origin point pixel value in a phase image generated from the acquired k-space data; c) extract physiological noise from the k-space data that was physiologically-induced by the subject using the global physiological fluctuation parameters; and d) remove the physiological noise from the MRI data prior to image reconstruction.

In one configuration, a method is provided for controlling physiologically-induced noise in functional magnetic resonance imaging (fMRI) data. The method includes acquiring blood-oxygen-level dependent (BOLD) fMRI k-space data of a subject with a repetition time that samples physiological motion, where the BOLD fMRI k-space data includes small local BOLD fMRI signals intermixed with physiological noise signals. The method also includes determining global physiological fluctuation parameters by extracting an origin point pixel value in a phase image generated from the acquired k-space data and extracting the physiological noise from the k-space data that was physiologically-induced by the subject using the global physiological fluctuation parameters. The physiological noise may be removed from the MRI data to recover the small local BOLD fMRI signals prior to reconstructing an image.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 3A depicts graphs of non-limiting example data before unwrapping in accordance with the present disclosure.

FIG. 3B depicts graphs of a non-limiting example data after unwrapping in accordance with the present disclosure.

FIG. 3C depicts graphs of a non-limiting example data after unwrapping and being placed in time order in accordance with the present disclosure.

DETAILED DESCRIPTION

Figure 1:
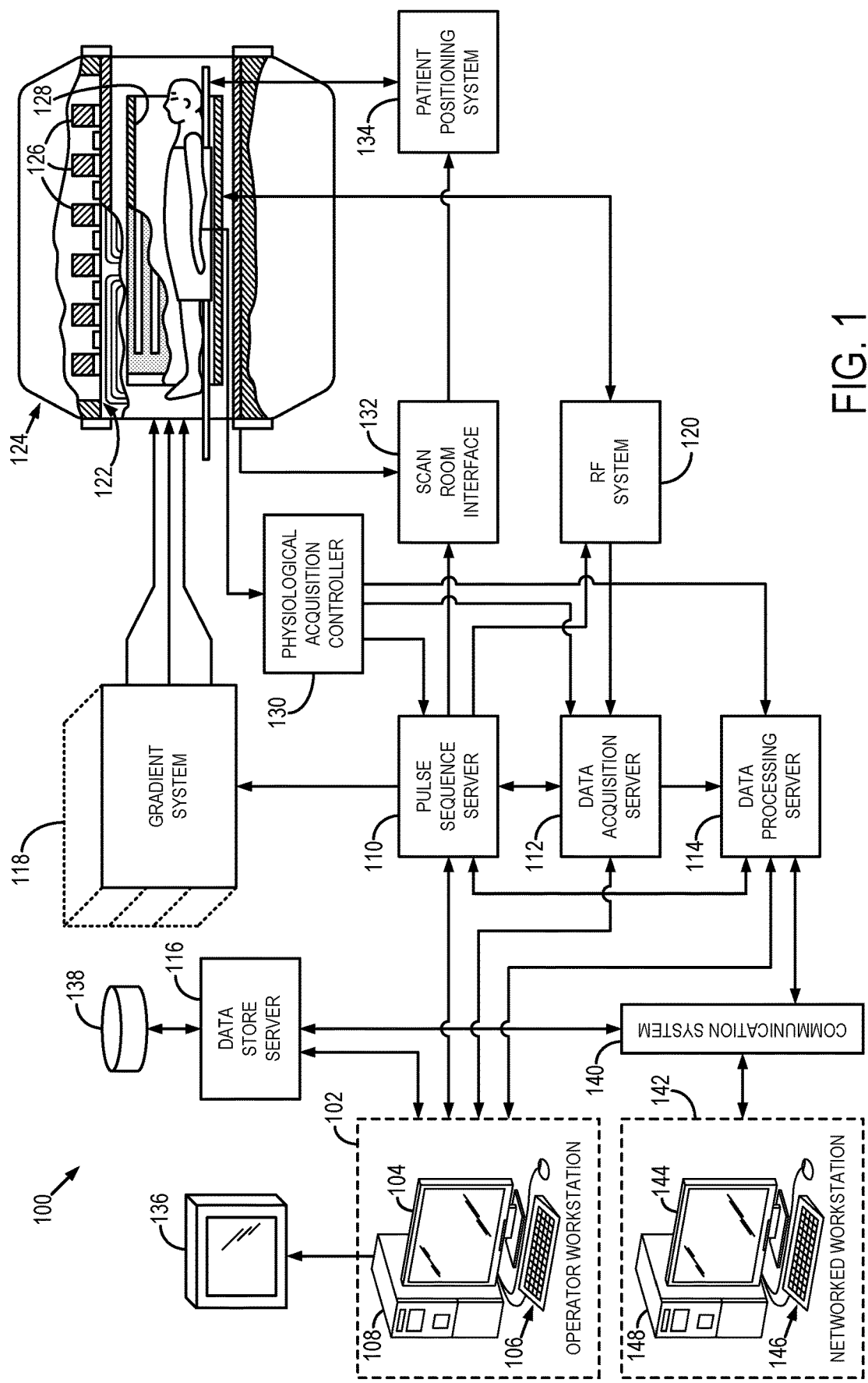
FIG. 1 is a block diagram of an example magnetic resonance imaging ("MRI") system configured with respect to systems and methods in accordance with the disclosure.

A system and method is provided for controlling physiological-noise in functional magnetic resonance imaging using raw k-space data to extract physiological noise effects. The method can identify these effects when they are separable and directly reflects the artefactual effects on the fMRI data, without the need for external monitoring/recording devices and to be compensated for via rigorous statistical analysis modeling of such noise sources. In some configurations, the physiological fluctuations may be treated as global perturbations presented around the origin point in a k-space 2D slice. In some configurations, each 2D slice may be acquired at a very short repetition time (compared to the 3D volume) with an effective sampling rate to sample cardiac and respiratory rhythms through proper reordering, detrending, and phase-unwarping techniques applied to the raw k-space data. Non-limiting example advantages of the present disclosure may include reduced fMRI scan duration for individual subjects and reduced sample size requirements in population studies, due to increased signal-to-Noise Ratio (SNR).

Functional magnetic resonance imaging (fMRI) technology provides an approach to study neuronal activity. Conventional fMRI detects changes in cerebral blood volume, flow, and oxygenation that locally occur in association with increased neuronal activity induced by functional paradigms. An MRI system is used to acquire signals from the brain over a period of time. As the brain performs a task, these signals are modulated synchronously with task performance to reveal which regions of the brain are involved in performing the task. The series of fMRI time course images must be acquired at a rate that is high enough to see the changes in brain activity induced by the functional paradigm. In addition, because neuronal activity may occur at widely dispersed locations in the brain, a relatively large 3D volume or multi-slice volume may be acquired in each time frame.

The systems and methods of the present disclosure may be used with any appropriate MR acquisition, such as an fMRI BOLD acquisition, diffusion weighted imaging (DWI), diffusion tensor imaging (DTI), echo planar imaging (EPI), and may use either a gradient echo (GRE) or spin echo (SE) sequence, and the like. In a non-limiting example, a fast 2D slice-wise sampling rate may be used to rapidly acquire data.

In some configurations, the systems and methods described in the present disclosure may be performed in a manner online with an imaging system's servers or computer systems, such that an imaging system's vendor or supplier may implement the systems and methods of the present disclosure without requiring any additional hardware. In other configurations, the systems and methods described in the present disclosure may be performed in an offline manner, where a computer system or server separate from an imaging system's servers or computer systems may be used. An online deployment may reduce the cost and overall time required to perform the method, whereas an offline deployment may be more easily adopted without involvement of an imaging system's vendor or supplier, and may allow for easier user customization to workflows or systems already in place.

Referring to FIG. 1, an example of an MRI system 100 that can implement the methods described here is illustrated. The MRI system 100 includes an operator workstation 102 that may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 110 may receive patient data from a physiological acquisition controller 130. By way of example, the physiological acquisition controller 130 may receive signals from a number of different sensors connected to the patient, including motion correction coil arrays (MOCCA), electrocardiograph ("ECG") signals from electrodes, pulse oximetry, or respiratory signals from a respiratory bellows or other respiratory monitoring devices. These signals may be used by the pulse sequence server 110, for example, to synchronize, or "gate," the performance of the scan with the subject's heart beat or respiration. Physiological acquisition controller 130 may be coupled to the pulse sequence server 110, the data acquisition server 112, the data processing server 114, or some combination thereof. In some configurations described in the present disclosure, physiological acquisition controller 130 may not be used and/or may not be present in the system. When the physiological controller 130 is not present or not used, physiological noise, such as cardiac and respiratory noise, may be removed using only the methods of the present disclosure.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

Subject-level noise in fMRI data acquisition can originate from a variety of sources. Some non-limiting examples include thermal noise, noise from scanner instability, patient motion (e.g., head motion), spin history, prototypical hemodynamic response function model error, cardiac and respiratory and $CO_2$ variability, and global fluctuations in fMRI signals. These noise sources can be at least partially controlled using individualized strategies applied to each specific source. For example, optimizing the scanning protocol and spatial smoothing can be used to attempt to control scanner-originated noise. As another example, spin history can be addressed using prospective motion control or via image correction and realignment. As further examples, hemodynamic response function model error can be mitigated by including temporal derivatives of HRF as nuisance repressors and cardiac and respiratory and $CO_2$ variability can be addressed with nuisance regressors. Finally, proportional scaling or further nuisance regressors can be used to address global fluctuations. However, as will be described, in some configurations, a subset of these sources of structured noise may be addressed in fMRI data in accordance with the present disclosure, such as by targeting physiological variations (cardiac, respiratory, and $CO_2$, for non-limiting examples).

In particular, the present disclosure recognizes that methods relying on external recording with resulting measures then incorporated as nuisance regressors may have several drawbacks. For example, one needs additional MRI-compatible equipment to acquire the physiological data alongside fMRI data acquisition to perform the external recordings. As another example, the external recorded physiological signals may not be accurately reflected due to interference effects from the scanning environment, and therefore may not be compensated for properly by using the recorded physiological signals as nuisance regressors at a subject-level analysis. Further still, the timing and the waveform of vessel pulsation and respiration peripherally does not necessarily correspond to the timing and the waveform of motion effects that occur in the brain and can obscure external recordings. That is, this difference in timing and the waveform between peripheral and central effects may not be constant, due to varying physiological parameters, limiting the ability to model for these timing differences accurately.

In some configurations, the interference effects may be extracted directly from raw data in k-space, such as raw multi-slice echo-planar imaging fMRI data, and the data may be incorporated as nuisance regressors after adequate steps of signal processing and nuisance regressor formation. The extraction procedure may include the consideration of a variety of information in various forms. In one non-limiting example, the physiological fluctuations may be relatively global, and therefore may be presented around the origin point in a k-space 2D slice. In another non-limiting example, each 2D slice may be acquired at a very short repetition time (compared to the 3D volume), and therefore has an effective sampling rate to sample cardiac and respiratory rhythms through proper reordering and phase-unwarping techniques applied to the raw k-space data.

The origin point may be determined by the type of coil used, such as a single channel birdcage coil generating a signal at a central k-space location. Other coils may also be used and may generate signal at locations other than a central location, which require setting an origin point away from a central location. In these configurations, a maximum signal location may be determined and the origin point may be adjusted to coincide with the maximum signal location.

Figure 2:
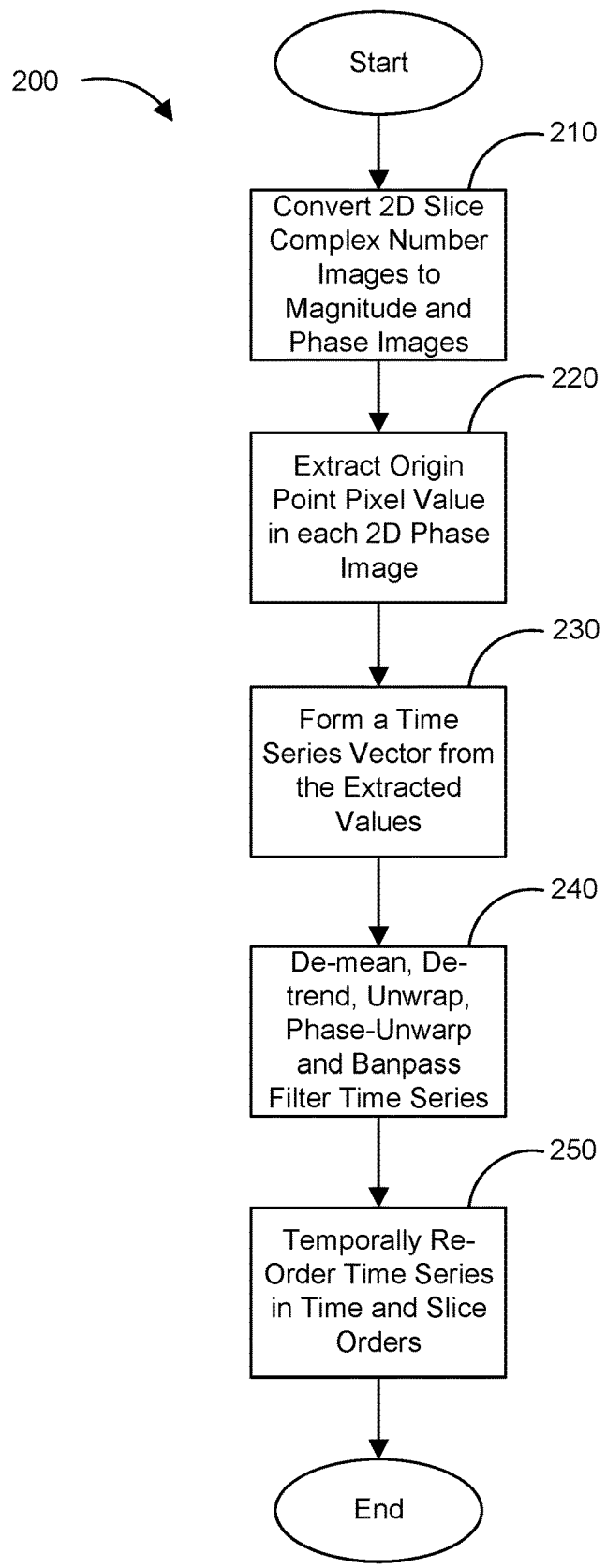
FIG. 2 is a flow chart setting forth some non-limiting examples of steps for a method in accordance with the present disclosure.

Referring to FIG. 2, a flow chart setting forth some non-limiting examples of steps for extracting and processing physiological noise effects from the raw k-space data is shown. The extracting and processing physiological noise effects method 200 includes converting 2D slice complex number images in k-space into the corresponding 2D slice-wise magnitude and phase images in k-space at step 210. In some examples, the origin point (one of the four pixels, or the mean of the four pixels, at the center of a matrix) of the phase image may be more contaminated by physiological noise effects than the one from the magnitude image. The pixel-value of the origin point in each 2D slice-wise phase image in k-space is then extracted at step 220. This value may be used to form a time series vector at step 230 (in a non-limiting example, a 1×number of slices in dimension) with a temporal resolution (such as based upon repetition time/number of slices), to be entered into a multi-step processing routine to be de-meaned, de-trended, unwrapped, phase-unwrapped and bandpass filtered empirically at step 240, and temporally reordered in both directions of time and slice orders at step 250. In some configurations, step 240 may be repeated, such as once or a plurality of times until a desired level of signal separation is achieved. The processed time series may be shown to a user and/or analyzed using a power spectrum. In some configurations, respiratory peaks with reduced aliasing respiratory sidebands of the cardiac peak may be shown in its power spectrum.

Referring to FIGS. 3A-G, a non-limiting example is shown for extracting and processing physiological noise effects from raw k-space fMRI BOLD multi-slice gradient-echo echo-planar imaging data. A large existing database of 550 fMRI scans, was used to improve, implement, and test a physiological noise extraction and compensation technique and algorithm based on k-space raw data according to the present disclosure. The noise extraction and compensation technique enabled detection of relatively small local BOLD fMRI signals with noise reduction incorporated as nuisance regressors, without the need for external monitoring or recording. 11 subjects in the non-limiting example include: ns=24 slices, TR=2000 ms, TE=35 ms, flip angle=80, matrix=64×64, FoV=220 mm, contiguous slice thickness=6 mm, 180 consecutive 3D volumes, resulting in 4320 2D slices. The temporal resolution was 83 ms (2000 ms/24 slices), and the time series vector was 1×4320 in dimension. In this non-limiting example data set, there were 5 extra volumes acquired before and after the experiment duration of 360 seconds, resulting in 190 3D volumes, 4560 2D slices.

Referring to FIG. 3A, a non-limiting example is shown of data before unwrapping. Referring to FIG. 3B, a non-limiting example is shown of data after unwrapping. Referring to FIG. 3C, a non-limiting example is shown of data after unwrapping and placed in time order. The top panels depict data over the number of slices, and the bottom panels are over volume.

Figure 3D:
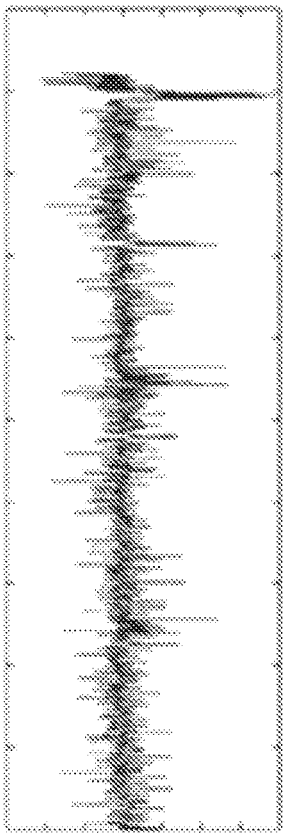
FIG. 3D depicts a graph of a non-limiting example time series slices by the acquisition time order after detrending in accordance with the present disclosure.
Figure 3E:
FIG. 3E depicts a graph of a non-limiting example power spectrum magnitude versus frequency after detrending in accordance with the present disclosure.

Referring to FIGS. 3D-3E, a non-limiting example is shown of data after slice de-trending. FIG. 3D depicts the time series over the number of slices. FIG. 3E depicts the power spectrum magnitude versus frequency (Hz). Non-limiting examples of the respiratory peak 310, cardiac peaks 320, and aliasing peaks 330 are depicted in the power spectrum.

Figure 3F:
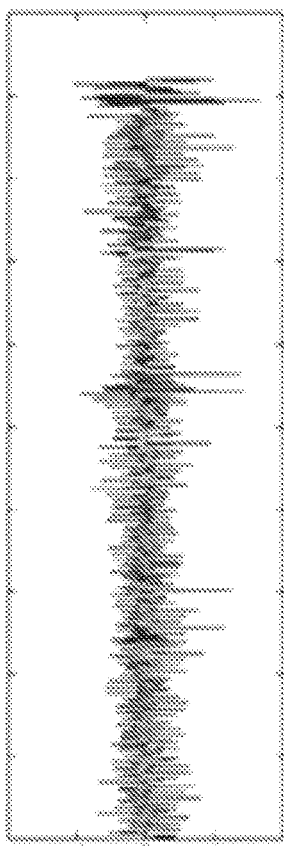
FIG. 3F depicts a graph of a non-limiting example time series slices by the acquisition time order after phase-unwarping and bandpass filtering in accordance with the present disclosure.
Figure 3G:
FIG. 3G depicts a graph of a non-limiting example power spectrum magnitude versus frequency after phase-unwarping and bandpass filtering in accordance with the present disclosure.

Referring to FIGS. 3F-3G, a non-limiting example is shown of data after phase-unwarp (to limit the values of the time series to $[-\pi, \pi]$) and bandpass filtering. FIG. 3F depicts the time series over the number of slices. FIG. 3G depicts the power spectrum magnitude versus frequency (Hz). Non-limiting examples of the respiratory peak 310 and cardiac peaks 320 are depicted in the power spectrums.

Figure 3J:
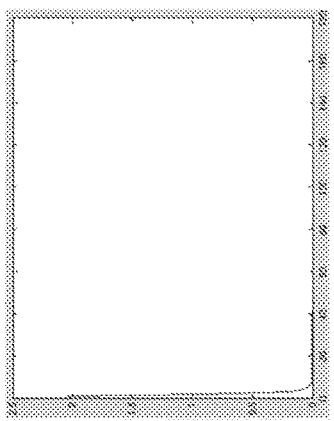
FIG. 3J depicts a non-limiting example graph of eigenvalues corresponding to the eigenvectors from FIG. 3I.
Figure 3I:
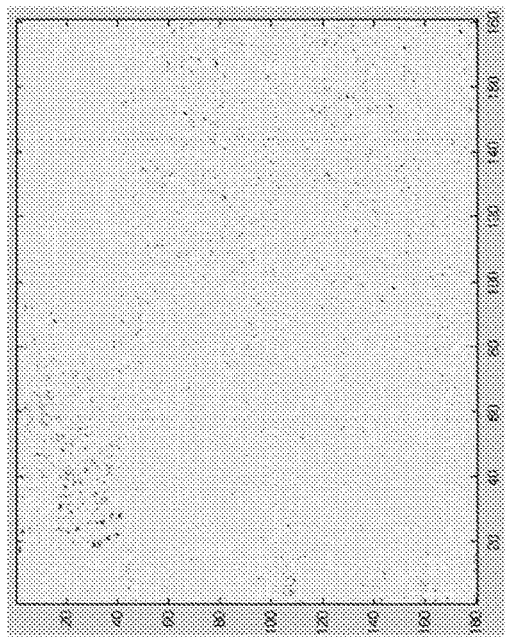
FIG. 3I depicts a non-limiting example graph of eigenvectors resulting from a principal component analysis performed on a matrix in FIG. 3H, sorted in descending order based on the corresponding eigenvalues in FIG. 3J.
Figure 3L:
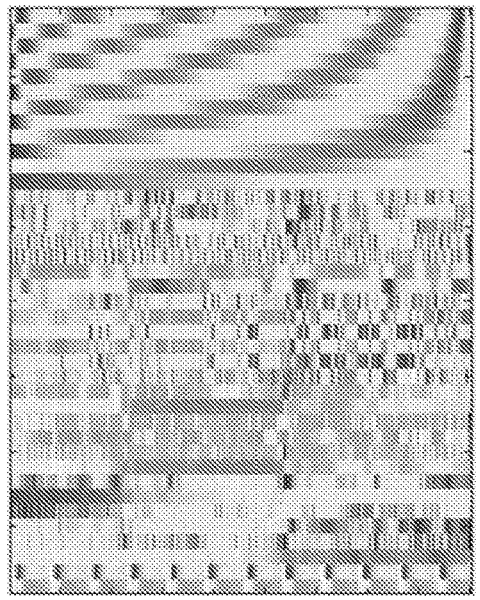
FIG. 3L depicts a non-limiting example of a design matrix that may be formed for a general linear model with the main regressors and the covariates of no interest in statistical analysis of processed fMRI data.
Figure 3H:
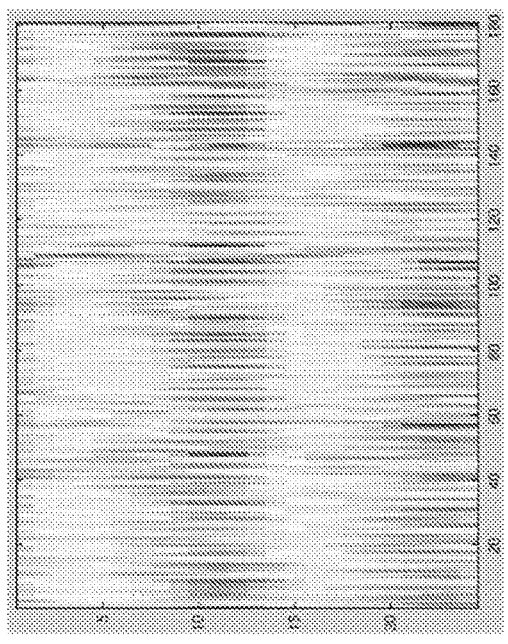
FIG. 3H depicts a non-limiting example graph of a matrix that may be formed of slice by volume from a processed time series vector.
Figure 3K:
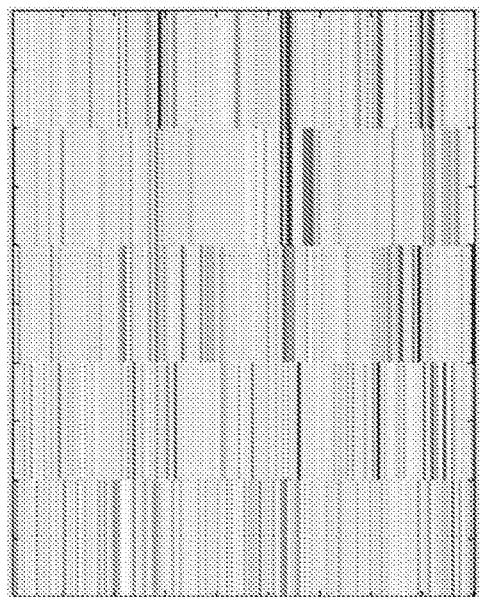
FIG. 3K depicts a non-limiting example graph of main eigenvectors.

Referring to FIG. 3H, a non-limiting example of a matrix graph is shown for a matrix that may be formed of slice by volume from a processed time series vector, such as described at step 455 below in FIG. 4. Referring to FIG. 3I, a non-limiting example graph is shown of the eigenvectors result from a principal component analysis performed on a matrix in FIG. 3H, sorted in descending order based on the corresponding eigenvalues in FIG. 3J, such as described at step 460 in FIG. 4 below. Referring to FIG. 3J, a non-limiting example graph of eigenvalues corresponding to the eigenvectors from FIG. 3I is shown, such as described at step 460 in FIG. 4 below. Referring to FIG. 3K, a non-limiting example graph of the main eigenvectors is shown. The main eigenvectors, such as the first 5 eigenvectors, may cover more than 90% of the explained variance and may be selected as covariates of no interest and incorporated into the design matrix, such as the design matrix of FIG. 3L, for statistical analysis of the processed fMRI data, such as described at step 465 in FIG. 4 below. Referring to FIG. 3L, a non-limiting example of a design matrix is shown and may be formed for a general linear model with the main regressors and the covariates of no interest in statistical analysis of the processed fMRI data, such as described at step 475 in FIG. 4 below.

Figure 4:
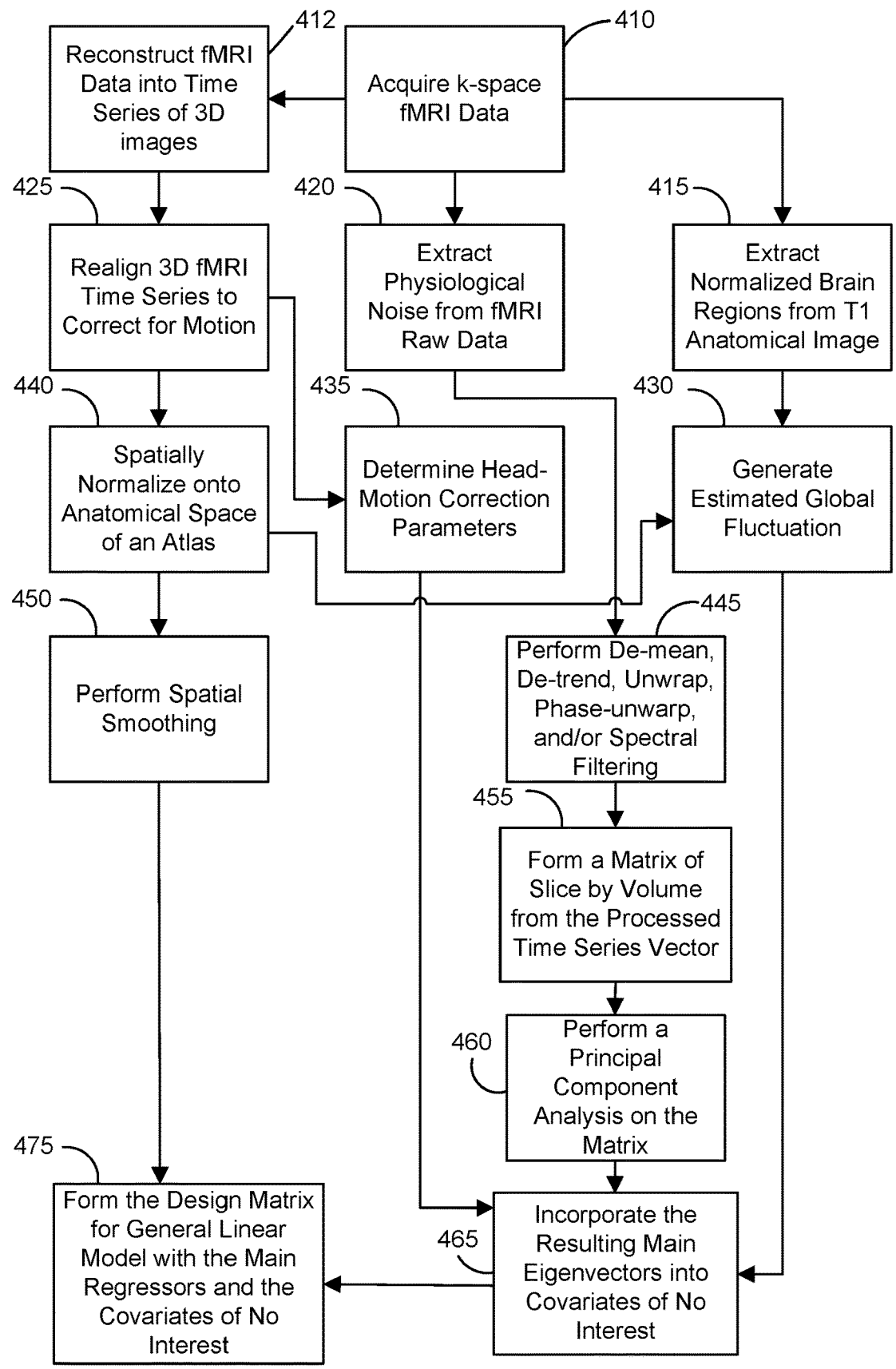
FIG. 4 is another flow chart setting forth some non-limiting examples of steps for a method in accordance with the present disclosure.

Referring to FIG. 4, a flow chart depicting non-limiting examples of subject-level statistical analysis of fMRI data that incorporates the method of compensating for the physiological noise effects is shown. The acquisition of k-space fMRI data is shown at step 410. The major noise sources, such as physiological noise, head motion, global fluctuation, and the like, are extracted with data-driven approaches, and modeled as nuisance regressors in a subject-level design matrix at step 475. This design matrix is formed at step 475 and may be composed of main regressors and covariates of no interest. An expression for the time series data of a voxel in the smoothed images y, design matrix P, estimation parameters $\beta$, and residuals E may be of the form in a general linear model:

$$\vec{y} = P \times \vec{\beta} + \vec{\varepsilon} \qquad (3)$$

fMRI data may be reconstructed into time series of 3D images in real space at step 412. Realignment of 3D fMRI time series, such as an EPI time series, may be performed at step 425 to correct for motion. Motion correction parameters, such as head motion correction parameters are determined at step 435. These parameters may be used to generate covariates of no interest at step 465.

Spatial normalization onto an anatomical space of an atlas, such as a human brain atlas, may be performed at step 440. Spatial smoothing may be performed at step 450, such as with a 3D Gaussian kernel. Normalized regions, such as normalized brain regions, are extracted at step 415 and may be from a T1 anatomical image. These regions may be used to generate an estimated global fluctuation based on the normalized 3D fMRI time series from step 440 at step 430. Covariates of no interest are generated at step 465 based partly upon the estimated global fluctuations.

Physiological noise is extracted from the fMRI raw data at step 420, such as by the non-limiting examples of FIG. 2. Unwrapping, detrending, phase-unwarping, spectral filtering, and/or some combination thereof for the data may be performed at step 445.

At step 455, arranging the processed time series described above from its vector form (1×n; in the non-limiting example of FIGS. 3A-3G, 1×4320) into the matrix form (ns×nv, The Number of Slices per 3D Volume×The Number of 3D Volumes; in the non-limiting example of FIG. 3H, 24×180). A Principal Component Analysis of the matrix in FIG. 3H may be conducted at step 460 and results in eigenvectors with corresponding eigenvalues (in the non-limiting example of FIGS. 3I-3J, 180 eigenvectors with 180 corresponding eigenvalues). Selected eigenvectors are then incorporated into covariates of no interest at step 465 (in the non-limiting example of FIGs. 3A-3K, 5 main eigenvectors were selected as 5 covariates). The design matrix P in (3) as shown in FIG. 3L may be formed for a general linear model with the selected regressors and the covariates of no interest at step 475. The design matrix P may be formed of subject-level statistical analysis of fMRI data to compensate for the physiological noise effects.

The present disclosure has described one or more preferred embodiments, and it should be appreciated that many equivalents, alternatives, variations, and modifications, aside from those expressly stated, are possible and within the scope of the invention.

The invention claimed is:

1. A method for controlling physiologically-induced noise in magnetic resonance imaging (MRI) data, comprising:
   a) acquiring MRI k-space data of a subject with a repetition time that samples physiological motion;
   b) determining global physiological fluctuation parameters by extracting an origin point pixel value in a phase image generated from the acquired k-space data;
   c) extracting physiological noise from the k-space data that was physiologically-induced by the subject using the global physiological fluctuation parameters; and
   d) removing the physiological noise from the MRI data using statistical modeling.

2. The method of claim 1, wherein extracting physiological noise includes converting complex number images into separate magnitude and phase images.

3. The method of claim 1, further comprising forming a time series vector from the extracted origin point pixel value in the phase image.

4. The method of claim 3, further comprising performing at least one of de-meaning, de-trending, and unwrapping the time series vector.

5. The method of claim 4, further comprising temporally reordering the time series in time and slice orders.

6. The method of claim 4, wherein a noise source is identified in a power spectrum of the time series after phase-unwarping and bandpass filtering.

7. The method of claim 1, wherein extracting physiological noise includes realigning 3D fMRI time series data to correct for motion, and
spatially normalizing the realigned data onto an anatomical space of a brain atlas.

8. The method of claim 7, further comprising spatially smoothing the realigned data using a 3D Gaussian kernel.

9. The method of claim 1, further comprising performing a principle component analysis on a matrix formed from the extracted physiological noise data.

10. The method of claim 9, wherein the principle component analysis generates main eigenvectors, and
wherein the main eigenvectors are used to remove the physiological noise.

11. A system for controlling physiologically-induced noise in magnetic resonance imaging (MRI) data, comprising:
a computer system configured to:
a) acquire MRI k-space data of a subject with a repetition time that samples physiological motion;
b) determine global physiological fluctuation parameters by extracting an origin point pixel value in a phase image generated from the acquired k-space data;
c) extract physiological noise from the k-space data that was physiologically-induced by the subject using the global physiological fluctuation parameters; and
d) remove the physiological noise from the MRI data using statistical modeling.

12. The system of claim 11, wherein extracting physiological noise includes converting complex number images into separate magnitude and phase images.

13. The system of claim 11, wherein the computer system is further configured to form a time series vector from the extracted origin point pixel value in the phase image.

14. The system of claim 13, wherein the computer system is further configured to perform at least one of de-meaning, de-trending, and unwrapping of the time series vector.

15. The system of claim 14, wherein the computer system is further configured to temporally reorder the time series in time and slice orders.

16. The system of claim 14, wherein a noise source is identified in a power spectrum of the time series after phase-unwarping and bandpass filtering.

17. The system of claim 11, wherein extracting physiological noise includes realigning 3D fMRI time series data to correct for motion, and
spatially normalizing the realigned data onto an anatomical space of a brain atlas.

18. The system of claim 17, wherein the computer system is further configured to spatially smooth the realigned data using a 3D Gaussian kernel.

19. The system of claim 11, wherein removing the physiological noise includes performing a principle component analysis on a matrix formed from the extracted physiological noise data.

20. The system of claim 19, wherein the principle component analysis generates main eigenvectors, and
wherein the main eigenvectors are used to remove the physiological noise.

21. A method for controlling physiologically-induced noise in functional magnetic resonance imaging (fMRI) data, comprising:
a) acquiring blood-oxygen-level dependent (BOLD) fMRI k-space data of a subject with a repetition time that samples physiological motion, the BOLD fMRI k-space data including small local BOLD fMRI signals intermixed with physiological noise signals;
b) determining global physiological fluctuation parameters by extracting an origin point pixel value in phase images generated from the acquired k-space data;
c) extracting the physiological noise from the k-space data that was physiologically-induced by the subject using the global physiological fluctuation parameters; and
d) removing the physiological noise from the MRI data to recover the small local BOLD fMRI signals using statistical modeling.

22. The method of claim 21, wherein removing the physiological noise includes:
determining head motion correction parameters,
generating estimated global fluctuation data, and
removing the physiological noise by generating nuisance regressors based upon: the extracted physiological noise data, the determined head motion correction parameters, and the generated global fluctuation data.

23. The method of claim 21, wherein extracting physiological noise includes converting complex number images into separate magnitude and phase images.

24. The method of claim 21, further comprising forming a time series vector from the extracted origin point pixel value in the phase images.

25. The method of claim 24, further comprising performing at least one of de-meaning, de-trending, and unwrapping the time series vector.

26. The method of claim 25, further comprising temporally reordering the time series in time and slice orders.

27. The method of claim 25, wherein a noise source is identified in a power spectrum of the time series after phase-unwarping and bandpass filtering.

28. The method of claim 21, wherein extracting physiological noise includes realigning 3D fMRI time series data to correct for motion, and
spatially normalizing the realigned data onto an anatomical space of a brain atlas.

29. The method of claim 28, further comprising spatially smoothing the realigned data using a 3D Gaussian kernel.

30. The method of claim 21, wherein removing the physiological noise includes performing a principle component analysis on a matrix formed from the extracted physiological noise data.

31. The method of claim 30, wherein the principle component analysis generates main eigenvectors, and
wherein the main eigenvectors are used to remove the physiological noise using statistical modeling.

* * * * *

UNITED STATES PATENT AND TRADEMARK OFFICE
CERTIFICATE OF CORRECTION

| | |
|---|---|
| PATENT NO. | : 11,630,176 B2 |
| APPLICATION NO. | : 17/788340 |
| DATED | : April 18, 2023 |
| INVENTOR(S) | : David Silbersweig et al. |

It is certified that error appears in the above-identified patent and that said Letters Patent is hereby corrected as shown below:

In the Specification

Column 9, Line 61, "E" should be --$\varepsilon$--.

Signed and Sealed this
Fourth Day of July, 2023

Katherine Kelly Vidal
*Director of the United States Patent and Trademark Office*